(12) United States Patent
Mase et al.

(10) Patent No.: US 9,050,386 B2
(45) Date of Patent: Jun. 9, 2015

(54) ANTIMICROBIAL RAW MATERIAL AND METHOD FOR MANUFACTURING THE SAME, AND ANTIMICROBIAL MATERIAL

(75) Inventors: Hiroshi Mase, Kisarazu (JP); Koji Hirota, Miura-gun (JP)

(73) Assignee: MITSUI CHEMICALS, INC., Tokyo (JP)

( * ) Notice: Subject to any disclaimer, the term of this patent is extended or adjusted under 35 U.S.C. 154(b) by 241 days.

(21) Appl. No.: 13/394,907

(22) PCT Filed: Sep. 7, 2010

(86) PCT No.: PCT/JP2010/005490
§ 371 (c)(1),
(2), (4) Date: Mar. 8, 2012

(87) PCT Pub. No.: WO2011/030538
PCT Pub. Date: Mar. 17, 2011

(65) Prior Publication Data
US 2012/0171406 A1    Jul. 5, 2012

(30) Foreign Application Priority Data
Sep. 8, 2009   (JP) ................. 2009-206818

(51) Int. Cl.
*C23C 14/06*     (2006.01)
*B32B 15/08*     (2006.01)
(Continued)

(52) U.S. Cl.
CPC .............. *A61L 15/46* (2013.01); *Y10T 428/265* (2015.01); *Y10T 428/2958* (2015.01);
(Continued)

(58) Field of Classification Search
CPC ....... B32B 5/26; H01L 23/293; H01L 23/295; H05K 3/284; B29K 2309/08; G11B 5/72; C08J 7/047; C23C 30/005
USPC .............. 428/76, 336, 389; 442/123; 427/250
See application file for complete search history.

(56) References Cited

U.S. PATENT DOCUMENTS

| 4,009,947 A | 3/1977 | Nishida et al. |
| 6,565,913 B2 * | 5/2003 | Arps et al. ................... 427/2.24 |

(Continued)

FOREIGN PATENT DOCUMENTS

| JP | 49-107547 | 10/1974 |
| JP | 60-12950 A | 1/1985 |

(Continued)

OTHER PUBLICATIONS

Machine_English_Translation_JP_2006342418_A; Kanematsu, Hideyuki; Sn—Cu Alloy Thin Film Having Antibacterial Property; Dec. 21, 2006; JPO; whole document.*

(Continued)

*Primary Examiner* — Tahseen N Khan
(74) *Attorney, Agent, or Firm* — Buchanan, Ingersoll & Rooney PC

(57) ABSTRACT

Provided is an antimicrobial raw material having excellent antibacterial and corrosion-resistance properties, which can be directly formed as a film even on a plastic substrate with low heat-resistance or a substrate whereof the color or properties are likely to change due to heat, and this can be achieved at relatively low cost. The antimicrobial raw material is a laminated structure which comprises a substrate layer and a copper-tin alloy layer disposed on the substrate layer, and which has a thickness ranging from 5 nm to 200 nm. The substrate layer is made of resin, natural fiber, or paper, the resin having the deflection temperature under load being 115° C. or lower when measured in accordance with ASTM-D648-56 under a load of 1820 kPa. The copper-tin alloy layer contains over 60 at % but no more than 90 at % of copper and 10 at % or more but less than 40 at % of tin.

11 Claims, 3 Drawing Sheets

(51) Int. Cl.
  *B32B 15/12* (2006.01)
  *B32B 27/06* (2006.01)
  *B32B 29/06* (2006.01)
  *B32B 3/02* (2006.01)
  *C23C 14/24* (2006.01)
  *A61L 15/46* (2006.01)
  *A61L 15/18* (2006.01)
  *C22C 9/02* (2006.01)
  *C23C 14/20* (2006.01)
  *A01N 59/20* (2006.01)

(52) U.S. Cl.
  CPC ............. *Y10T 428/239* (2015.01); *A61L 15/18* (2013.01); *A61L 2300/102* (2013.01); *A61L 2300/404* (2013.01); *C22C 9/02* (2013.01); *C23C 14/20* (2013.01); *A01N 59/20* (2013.01)

(56) References Cited

U.S. PATENT DOCUMENTS

2004/0043686 A1* 3/2004 Batdorf .......... 442/123
2009/0264028 A1* 10/2009 Chuma .......... 439/876

FOREIGN PATENT DOCUMENTS

| JP | 61-182943 A | 8/1986 |
|---|---|---|
| JP | 4-228550 A | 8/1992 |
| JP | 8-41611 A | 2/1996 |
| JP | 9-111378 A | 4/1997 |
| JP | 9-505112 A | 5/1997 |
| JP | 10-110268 A | 4/1998 |
| JP | 11-179870 A | 7/1999 |
| JP | 2947934 B2 | 9/1999 |
| JP | 2003171602 A * | 6/2003 |
| JP | 2004-183030 A | 7/2004 |
| JP | 2006-152353 A | 6/2006 |
| JP | 2006-342418 A | 12/2006 |
| JP | 2006342418 A * | 12/2006 |

OTHER PUBLICATIONS

Machine_English_Translation_JP_2003171602_A; Shimatani, Hiroyuki; Antibacterial Photocatalytic Coating Material and Member; Jun. 20, 2003; JPO; whole document.*

Extended European Search Report dated Feb. 6, 2013 in the corresponding European application 10815138.2 (9 pages).

International Search Report (PCT/ISA/210) issued on Dec. 14, 2010, by Japanese Patent Office as the International Searching Authority for International Application No. PCT/JP2010/005490.

International Preliminary Examination Report (PCT/IPEA/409) issued Oct. 20, 2011, by Japanese Patent Office as the International Searching Authority for International Application No. PCT/JP2010/005490.

* cited by examiner

ANTIMICROBIAL RAW MATERIAL AND METHOD FOR MANUFACTURING THE SAME, AND ANTIMICROBIAL MATERIAL

TECHNICAL FIELD

The present invention relates to antimicrobial raw materials, methods for producing the same, and antimicrobial materials.

BACKGROUND ART

To keep articles in sanitary condition, antimicrobial substances are applied to their surface under certain circumstances. For example, in food-handling facilities, domestic kitchens and medical facilities, it is required to keep the surface of the interior floor and walls, instruments, fixtures or other articles germ-free in order to prevent possible contact infection or poisoning caused by harmful microorganisms such as bacterial pathogens attached to their surface. It is also required to effectively prevent mold growth or food spoilage in such places as house closets or food depositories, which are highly humid and less ventilated places, part of a building where water is circulated and thus condensation frequently forms (e.g., bathroom), and the inside of an air-conditioner or refrigerator. Thus, it has been required to impart a harmful microorganism reduction effect to the surface of articles such as building materials (e.g., wall paper), food storage containers, and bathroom accessories.

One widespread method of imparting a harmful microorganism reduction effect to the article surface is to incorporate therein an antimicrobial agent or apply thereon antimicrobial agent-containing coating. Antimicrobial agents are classified into organic and inorganic antimicrobial agents. In particular, inorganic antimicrobial agents such as silver ion-bearing zeolites are attracting attention because they have a wider spectrum of activity to harmful microorganisms than organic counterparts as well as are less toxic to the human body.

Moreover, some types of metals are known as a substance that has antimicrobial activity; in particular, silver, copper and alloys thereof are known. For preventing food poisoning and mold growth, these metals have been widely used for eating utensils, wash-basin, building materials, etc. Attempts have also been made to make use of the antimicrobial effect of copper and copper alloys for infection control medical facilities or other places (see Non-Patent Literatures 1 to 8). In fact, in some medical facilities, copper and copper alloys are used for metallic parts (e.g., doors), bed fences, etc.

However, articles having an organic antimicrobial agent incorporated therein or applied thereon do not necessarily have a satisfactory harmful microorganism reduction effect because the antimicrobial agent shows antimicrobial activity to only limited strains of microorganisms when used singly, because new strains of resistant microorganisms are more likely to emerge, and so forth.

Inorganic antimicrobial agents have a relatively superior effect of reducing harmful microorganism. However, in the case of articles prepared by incorporating inorganic antimicrobial agents into polymer materials, the antimicrobial agent is not necessarily exposed to the entire surface of the article, and therefore, there is a risk that a population of harmful microorganism attached to non-exposed part of the article is not affected by the agent and survives.

Examples of articles prepared by processing of an antimicrobial metal (e.g., silver or copper) itself include copper-made garbage boxes for sink (so-called triangular sink tidy) and brass fittings. Because these articles have disinfecting activity over the entire surface, there is no concern that such a case as described above—where a population of harmful microorganism present on the surface free from inorganic antimicrobial agent is not affected by the agent—will occur. Nevertheless, due to their high specific gravity, the obtained article becomes not only heavy, but costly. Moreover, articles made of silver or copper have the disadvantage of being susceptible to discoloration by contact with water, acid or salt, which makes their appearance poor.

Aiming to suppress such discoloration in metals, studies have been made on corrosion-resistant alloys, including bronze, which is composed primarily of copper with tin as the additive, aluminum bronze, which is composed primarily of copper and aluminum as the additive, and nickel silver, which is composed primarily of copper with nickel and zinc as the additives. It has been scientifically verified that some of the corrosion-resistant alloys have an antimicrobial effect (see Non-Patent Literatures 1 to 6). However, they are not widely used in view of production costs, weight, and processability.

For example, while bronze, a metal alloy composed primarily of copper with tin as the additive, is known to have higher corrosion resistance with increasing tin proportion, it becomes more brittle as the tin proportion increases and thus becomes less processable. For this reason, in the case of a plate or other form that requires subsequent processing, the highest possible tin proportion is about 5 wt % (about 3 atom %) based on copper, and in the case of a cast that requires no subsequent processing, the highest possible tin proportion is about 10 wt % (about 6 atom %) based on copper. Thus, there is limitation in increasing corrosion resistance. On the other hand, aluminum bronze (metal alloy composed primarily of copper and aluminum as the additive) and nickel silver (metal alloy composed primarily of copper with nickel and zinc as the additives) have superior corrosion resistance, but they are not widely used due to their relatively high production costs and high specific gravity of 8 or more.

In particular, as for products having on their surface an antimicrobial thin metal film, poor appearance is a serious problem. The surface of bulk copper or copper alloy is covered with a relatively stable oxide film with a thickness of the order of submicrons, which suppresses the progression of corrosion on their surface. On the other hand, articles having an antimicrobial thin metal film with a thickness comparable to that of such an oxide film cannot be stably fixed to a substrate article because the antimicrobial thin metal film undergoes rapid oxidation over the entire surface. Thus, copper or copper alloy thin films significantly degrade by contact with water compared to bulk copper or copper alloy. In particular, since a pure copper thin film is lost in a relatively short period of time by oxidization, when water droplets remain attached to part of an article covered with such a pure copper thin film, product quality significantly decreases due to the creation of yellow brown spots at the part.

Silver thin films, on the other hand, undergo oxidization sufficiently slowly upon contact with water and therefore raise no problem for practical applications. However, since silver films produce water-soluble silver chlorides upon contact with salts, they have the disadvantage that they undergo discoloration or are lost upon contact with sweat or other body fluid as with thin copper films, which significantly makes their appearance poor.

Various studies have been made on copper alloy thin films. For example, paper and plastic films having on their surface a metal thin film made of, for example, copper, silver or alloy containing copper and/or silver as an antimicrobial metal thin film are proposed (see Patent Literatures 1 to 7). In particular, as an antimicrobial metal thin film to be provided on substrates, a Sn—Cu alloy thin film containing Sn—Cu alloy and 1 to 10 wt % of $SnO_2$ is proposed (see Patent Literature 7). However, none of Patent Literatures 1 to 7 study a metal thin film that can suppress corrosion by water or salt without reducing antimicrobial activity, nor do they disclose a Sn amount that can realize such a film.

On the other hand, as an antimicrobial metal with improved corrosion resistance, an amorphous alloy is proposed which contains 15 atom % to 30 atom % of Ta, 15 atom % to 40 atom % of Cu, 20 atom % to 51 atom % of Fe, 2 atom % to 5 atom % of Ni, and 6 atom % to 14 atom % of Cr (see Patent Literature 8). As an amorphous alloy having antimicrobial activity, oxidization resistance, discoloration resistance and corrosion resistance, an alloy is proposed that contains 5 atom % or more of Ta and/or 15 atom % or more of Nb, as well as Ti and Ni, with the remaining portion substantially consisting of Cu (see Patent Literature 9).

These alloy thin films are formed by a variety of deposition methods. In general, when forming a metal thin film on a substrate like a plastic substrate, metal thin films made of pure metal (e.g., copper or silver) can be produced with relatively good productivity by vacuum deposition. It is difficult, however, to form alloy thin films containing two or more different metals by vacuum deposition. Thus, alloy thin films are typically manufactured for example by flash deposition—a relatively high-cost deposition process, by simultaneous vapor deposition—a deposition process in which two or more separate deposition sources are heated for deposition while being independently controlled, or by sputtering—a less productive deposition process.

It should be noted, however, that it has been suggested in the art that some combinations of metals can be evaporated to deposit an alloy thin metal film even when an alloy is employed as a single deposition source. For example, it has been proposed in the art to deposit a copper-tin alloy on a transparent substrate by heating of a 1:1 ratio copper-tin alloy on a molybdenum board (see Patent Literature 10). Moreover, aiming to improve corrosion resistance of a reflective metal film, it has also been proposed in the art to cover the reflective metal film with a deposited alloy film composed primarily of copper and tin (see Patent Literature 11).

CITATION LIST

Patent Literature

[PTL 1] Japanese Patent Application Laid-Open No. 11-179870

[PTL 2] Japanese Patent Application Laid-Open No. 2004-183030

[PTL 3] Japanese Patent Application Laid-Open No. 61-182943

[PTL 4] Japanese Patent No. 2947934

[PTL 5] Japanese Patent Application Laid-Open No. 09-505112

[PTL 6] Japanese Patent Application Laid-Open No. 2006-152353

[PTL 7] Japanese Patent Application Laid-Open No. 2006-342418

[PTL 8] Japanese Patent Application Laid-Open No. 08-41611

[PTL 9] Japanese Patent Application Laid-Open No. 04-228550

[PTL 10] Japanese Patent Application Laid-Open No. 60-12950

[PTL 11] Japanese Patent Application Laid-Open No. 49-107547

Non-Patent Literature

[NPL 1] J. O. Noyce, et al., Journal of Hospital infection, (British), Hospital Infection Society, 2006, vol. 63, p. 289-297

[NPL 2] J. O. Noyce, et al., Applied and Environmental Microbiology, (US), American Society for Microbiology, 2007, vol. 73, no. 8, p. 2748-2750

[NPL 3] C. E. Santo, et al., Applied and Environmental Microbiology, (US), American Society for Microbiology, 2008, vol. 71, no. 4, p. 977-986

[NPL 4] J. O. Noyce, et al., Applied and Environmental Microbiology, (US), American Society for Microbiology, 2006, vol. 72, no. 6, p. 4239-4244

[NPL 5] S. A. Wilks, et al., International Journal of Food Microbiology, International Union of Microbiological Societies, 2005, vol. 105, p. 445-454

[NPL 6] L. Weaver, et al., Journal of Hospital Infection, (British), Hospital Infection Society, 2008, vol. 68, p. 145-151

[NPL 7] S. Kubota, Research Report of the Toyama Industrial Technology Center, (1997), p. 11-73-74

[NPL 8] Niiyama et.al, Japanese Journal of Dermatology, Japanese Dermatological Association, 2009, vol. 119, p. 899-906

SUMMARY OF INVENTION

Technical Problem

The alloy thin films disclosed by Patent Literatures 8 and 9, however, are more expensive than copper thin films because they contain about 15 wt % of rare metal such as tantalum and/or niobium, which are ten times or more as expensive as copper. Moreover, tantalum and niobium have the disadvantage of being unable to be rapidly deposited by means of vacuum deposition, plating or other method due not only to their high melting point but to lower water solubility of their salts. For this reason, metal thin films that can be produced relatively inexpensively as well as have high antimicrobial activity and high corrosion resistance have not yet been available in the art.

Alloy thin films are formed by simultaneous vapor deposition or sputtering, with simultaneous vapor deposition being more preferable in view of cost, productivity etc. However, it has been difficult with simultaneous vapor deposition to deposit an alloy thin film with a controlled alloy composition. The simultaneous vapor deposition is classified into two types: 1) simultaneous vapor deposition in which alloy is deposited from a single deposition source, and 2) simultaneous vapor deposition in which an alloy is deposited from two or more separate deposition sources prepared for respective metal components. Alloy thin films prepared from the former process have the disadvantage that the alloy composition tends to greatly deviates from that of the deposition source. On the other hand, the latter process has the disadvantage that production cost tends to increase due to the necessity to control the heating temperature of two or more deposition sources independently.

Under these circumstances, alloy thin films are typically formed by laminating thin films made of different metals and subjecting the laminated film to annealing at high temperature. For example, the Sn—Cu alloy thin film disclosed by Patent Literature 7 is formed by laminating layers of Cu and Sn on a substrate to form multi-layer plating and subjecting it to heat treatment (annealing). High-temperature annealing has thus been required in the art for alloying of multi-layer plating consisting of layers of Cu and Sn. For this reason, it has heretofore been impossible to directly deposit alloy thin films onto low-heat resistant plastic substrates or substrates that are susceptible to thermal discoloration or thermal degradation (e.g., paper and natural fiber).

The present invention has been accomplished in view of the foregoing circumstances, and an object of the present invention is to provide a relatively inexpensive antimicrobial raw material with high antimicrobial activity and high corrosion resistance, which antimicrobial raw material is directly deposited onto a plastic film or a substrate which is susceptible to thermal discoloration or thermal degradation, a method for producing the antimicrobial raw material, and an antimicrobial material.

Solution to Problem

The inventors have established that high antimicrobial activity and high corrosion resistance can be achieved at the same time by adjusting the copper-tin alloying ratio within a particular range. The inventors also have established that by adjusting the copper-tin alloying ratio within a further particular range, it is possible to reduce, upon deposition of a copper-tin alloy film by simultaneous vapor deposition, deviation between the alloy composition of the deposition source and the alloy composition of the resultant film, and that this makes it possible to provide an alloy thin film with a controlled alloy composition range even when using a single alloy deposition source. Moreover, the inventors have established that alloy thin films produced from a single alloy deposition source have good adhesion to substrate layer. The inventors thus established that annealing for alloying thin metal films becomes unnecessary and alloy thin films can be directly deposited onto low-heat resistant plastic substrates or substrates that are susceptible to thermal discoloration or thermal degradation. The present invention has been accomplished based on these findings.

A first aspect of the present invention relates to antimicrobial raw materials and production methods given below.
[1] An antimicrobial raw material including:
a substrate layer made of resin, natural fiber or paper, the resin having a deflection temperature under load of 115° C. or below as measured in accordance with ASTM-D648-56 under a load of 1,820 kPa; and
a copper-tin alloy layer disposed on the substrate layer, the copper-tin alloy layer containing over 60 atom % to 90 atom % of copper and 10 atom % to less than 40 atom % of tin,
wherein the copper-tin alloy layer has a thickness of 5 nm to 200 nm.
[2] The antimicrobial raw material according to [1], wherein the copper-tin alloy layer contains 15 atom % to less than 40 atom % of tin, with the remaining portion substantially consisting of copper.
[3] The antimicrobial raw material according to [1] or [2], wherein the substrate layer is made of material selected from the group consisting of polyethylene terephthalate, polyethylene naphthalate, polyethylene, and polypropylene.
[4] The antimicrobial raw material according to any one of [1] to [3], wherein Q value ($\Omega$/(nm·Cu atom %)) is 0.001 to 0.007, the Q value being obtained by dividing a sheet resistance ($\Omega$) of the copper-tin alloy layer by a product of thickness of (nm) and copper atom content (Cu atom %) of the copper-tin alloy layer.
[5] An antimicrobial raw material including:
a substrate layer; and
a copper-tin alloy layer disposed on the substrate layer, the copper-tin alloy layer formed by simultaneous vapor deposition using an evaporation source composed of a copper-tin alloy containing over 60 atom % to 85 atom % of copper and 15 atom % to less than 40 atom % of tin, the copper-tin alloy layer having a thickness of 5 nm to 200 nm.
[6] The antimicrobial raw material according to any one of [1] to [5], wherein the copper-tin alloy layer covers the entire or part of an outermost surface of the antimicrobial raw material.
[7] The antimicrobial raw material according to any one of [1] to [6], wherein the antimicrobial raw material is a film, and when the film is 4 cm in width, 10 cm in length and 25 μm in thickness, an amount of curvature is 2 mm or less.
[8] The antimicrobial raw material according to any one of [1] to [7], wherein the substrate layer is a nonwoven fabric, woven fabric or yarn.
[9] A method for producing an antimicrobial raw material, including:
providing an evaporation source composed of an copper-tin alloy containing over 60 atom % to 85 atom % of copper and 15 atom % to less than 40 atom % of tin;
placing a substrate so as to face the evaporation source;
evaporating the copper-tin alloy from the evaporation source to generate a metal vapor; and
allowing the metal vapor to contact the substrate to deposit thereon a copper-tin alloy layer containing over 60 atom % to 90 atom % of copper and 10 atom % to less than 40 atom % of tin.
[10] The method according to [9], wherein the substrate is made of resin, natural fiber or paper, the resin having a deflection temperature under load of 115° C. or below as measured in accordance with ASTM-D648-56 under a load of 1,820 kPa.

A second aspect of the present invention relates to antimicrobial materials given below.
[11] An antimicrobial material including the antimicrobial raw material according to any one of [1] to [8].
[12] The antimicrobial material according to [11], wherein the antimicrobial material is used as a touch panel protection film.
[13] The antimicrobial material according to [11], wherein the antimicrobial material is used as medical material.
[14] The antimicrobial material according to [11], wherein the antimicrobial material is used as purification material.

Effects of Invention

According to the present invention, it is possible to relatively inexpensively provide an antimicrobial raw material which has high antimicrobial activity and high corrosion resistance and which can be directly deposited onto low-heat resistant plastic substrates.

DESCRIPTION OF EMBODIMENTS

1. Antimicrobial Raw Material

Figure 1:
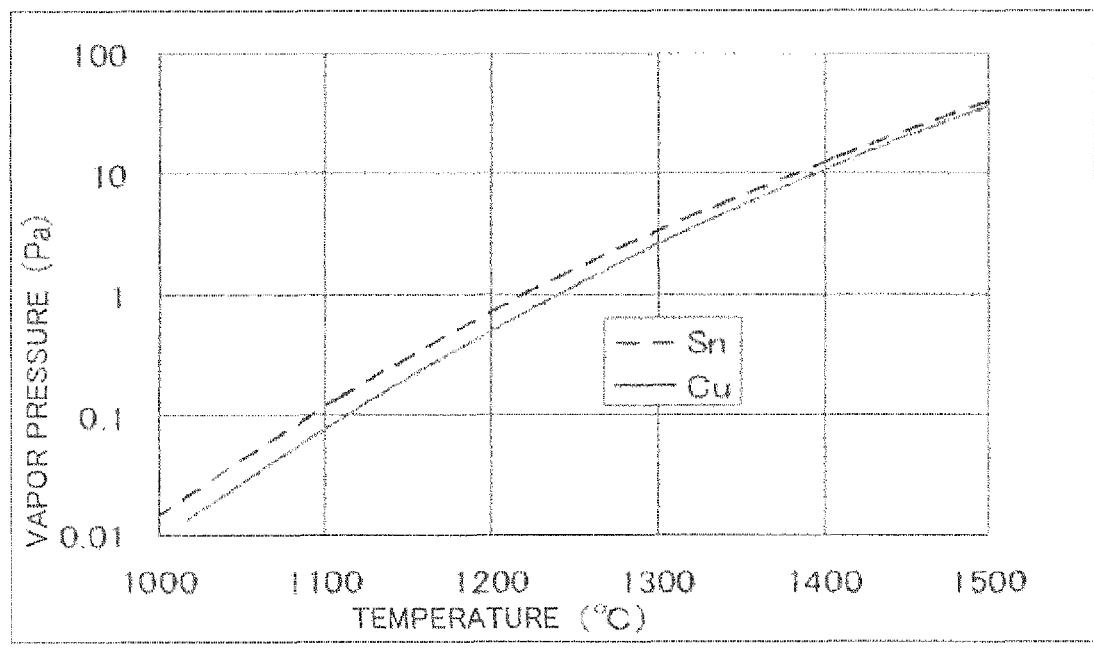
FIG. 1 is a graph showing temperature-dependence of vapor pressures of copper and tin.

An antimicrobial raw material of the present invention includes a substrate layer and a copper-tin alloy layer disposed on the substrate layer, and optionally includes additional layer(s) as needed.

There is no particular limitation on the substrate layer; it may be made of metal, glass, ceramics, resin (including synthetic fiber), natural fiber, paper, wood, etc. Among these materials, the substrate layer is preferably made of resin, natural fiber or paper in view of their good flexibility, good processability, low cost, etc.

There is no particular limitation on the resin used to constitute the substrate layer; it may be either thermoplastic resin or thermosetting resin. The resin used to constitute the substrate layer preferably has a deflection temperature under load of 115° C. or below, preferably 90° C. or below, as measured in accordance with ASTM-D648-56 under a load of 1,820 kPa. The reason for this is that resin with a deflection temperature under load of 115° C. or below has good processability and that resultant films also have good flexibility.

Deflection temperature under load is measured with a method that complies with ASTM-D-648-56. Specifically, deflection temperature under load can be measured as the temperature at which the bending strain of a test specimen, loaded on an apparatus for flatwise test and heated at a constant heating rate of 2° C./min, reaches 0.2% under a load of 1,820 kPa. The test specimen is 80 mm in length, 10 mm in width and 4 mm in thickness, and distance between grips may be set to 64 mm.

Examples of resins having a deflection temperature under load of 115° C. or below include polyester resins, polyolefin resins, and polyamide resins, with polyester resins and polyolefin resins being preferable. Examples of the polyester resins include polyethylene terephthalate and polyethylene naphthalate. The polyolefin resins may be homopolymers of α-olefins or copolymers of α-olefins and different comonomers. The α-olefin in the polyolefin resins may be, for example, ethylene or propylene. Examples of such polyolefin resins include polyethylene and polypropylene. Examples of the polyamide resins include nylon 6 and nylon 66.

The substrate layer may be a film, nonwoven fabric or woven fabric.

The thickness of the substrate layer may be, for example, about 5 μm to about 700 μm, although it depends on the intended application of the antimicrobial raw material. When the substrate layer is excessively thick, the antimicrobial raw material becomes heavy. When the substrate layer is excessively thin, the mechanical strength of the antimicrobial raw material decreases.

The copper-tin alloy layer is disposed on the substrate layer and has a function of imparting antimicrobial activity to the substrate layer. Accordingly, the copper-tin alloy layer is preferably disposed on the outermost surface of the antimicrobial raw material.

The copper-tin alloy layer preferably contains over 60 atom % to 90 atom % of copper and 10 atom % to less than 40 atom % of tin, more preferably contains 63 atom % to 90 atom % of copper and 10 atom % to 37 atom % of tin, most preferably contains 15 atom % to less than 40 atom % of tin with the remaining portion substantially consisting of copper. When the tin content in the copper-tin alloy is less than 10 atom %, it may result in appearance change due to corrosion or discoloration by contact with water, salt water, body fluid or other fluid. Antimicrobial activity increases with increasing copper content.

The copper-tin alloy layer may contain additional element(s) as long as the above copper content and tin content are satisfied. In this way economic efficiency, affinity for liquids, affinity for substrates, color tone of the metal thin film, etc., may be adjusted. For example, the copper-tin alloy may contain such metals as aluminum, germanium, berylium, nickel and/or silicon, which have vapor pressures close to that of copper in melted state. The copper-tin alloy layer may also contain additional antimicrobial metals such as zinc, silver and/or nickel, as long as corrosion resistance does not decrease.

Alloying of copper with tin for improved corrosion resistance has been widely conducted in the field of bulk metal materials. However, even today, the upper limit of the tin content in copper-tin alloy, which has been used as bronze since ancient times, is about 10 atom %. Copper-tin alloys that contain greater than 10 atom % of tin become more brittle. Thus, although such copper-tin alloys may be used as a cast metal, they are not usually used as plate or rod material that is subsequently subjected to plastic working process.

Since the copper alloy in the antimicrobial raw material of the present invention is provided in the form of thin film disposed on the substrate layer, even when a copper-tin alloy containing greater than 10 atom % of tin is used, the antimicrobial raw material has processability and durability during use.

There is no particular limitation on the thickness of the copper-tin alloy layer, and it is only necessary that desired antimicrobial activity can be ensured. The thickness is preferably 200 nm or less, more preferably 100 nm or less. When making the copper-tin alloy layer translucent, the thickness is preferably 50 nm or less, more preferably 30 nm or less. The thickness of the copper-tin alloy layer is preferably 5 nm or more, more preferably 10 nm or more. This is to entirely cover the surface of the substrate layer with the copper-tin alloy layer as well as to obtain uniform antimicrobial activity.

When the substrate layer is provided as woven fabric, nonwoven fabric or the like, the deposition amount of the copper-tin alloy is preferably 1.0 m g/mm$^2$ or less, more preferably 0.5 mg/mm$^2$ or less. When making the copper-tin alloy layer translucent, the deposition amount of copper-tin alloy is preferably 0.25 mg/mm$^2$ or less, more preferably 0.15 mg/mm$^2$ or less. The deposition amount of copper-tin alloy is preferably 0.025 mg/mm$^2$ or more, more preferably 0.05 mg/mm$^2$ or more. This is to entirely cover the surface of the substrate layer with the copper-tin alloy layer as much as possible as well as to obtain uniform antimicrobial activity.

Q value ($\Omega$/(nm·Cu atom %)), which is obtained by dividing sheet resistance ($\Omega$) of the copper-tin alloy layer by a product of its thickness (nm) and copper atom content (Cu atom %) therein, is preferably 0.001 to 0.007, more preferably 0.003 to 0.005. When Q value of the copper-tin alloy layer is less than 0.001, the density of the copper-tin alloy layer is so low that film strength may become inadequate. When Q value of the copper-tin alloy layer is greater than 0.007, the density of the copper-tin alloy layer is so high that the resultant antimicrobial raw material tends to less flexible. In order for Q value of the copper-tin alloy layer to fall within the above range, for example, the copper-tin alloy layer is preferably formed by vapor deposition rather than sputtering.

The antimicrobial raw material of the present invention may further include an adhesive layer on the surface of the substrate layer opposite from that on which the copper-tin alloy layer is formed. The adhesive layer is preferably such that it allows the antimicrobial raw material once applied to the article surface to be detached (releasable adhesive layer). The reason for this is that the antimicrobial raw material needs to be detached in such cases where antimicrobial activity and other properties have deteriorated due to attachment of dust on the surface of the copper-tin alloy layer, or where appearance has been impaired.

There is no particular limitation on the type of the adhesive agent used for the adhesive layer; any of rubber adhesive agents, acrylic adhesive agents, silicone adhesive agents, urethane adhesive agents and other adhesive agents may be used.

The antimicrobial raw material of the present invention may include additional layer(s) as needed. The additional layer may be a layer having water absorbability, water repellency, light scattering property, surface smoothness, good appearance (e.g., color or gloss) or other property.

When the antimicrobial raw material is provided as a film, the amount of curvature is preferably 2 mm or less, more preferably 1.5 mm or less, as measured when the film dimension is 4 cm in width, 10 cm in length and 25 µm in thickness. The amount of film curvature is measured as the amount of curvature from the surface of the film prior to thin film deposition after allowing the thin-film deposited film to stand at 23C.° at 50% RH for 24 hours. As will be described later, since the antimicrobial raw material of the present invention can be prepared without high-temperature annealing, it has the advantage of smaller amount of warpage.

2. Method for Producing Antimicrobial Raw Material

An antimicrobial raw material of the present invention can be produced by a step of depositing a copper-tin alloy layer on one side of a substrate layer.

There is no particular limitation on the method of forming the copper-tin alloy layer. As for physical deposition methods, vacuum deposition, ion plating, sputtering, laser deposition, arc deposition, spraying, hot dip coating, etc., can be exemplified. As for chemical deposition methods, electroplating, electroless plating, plasma CVD, thermal CVD, etc., can be used.

Of these thin-film deposition methods, vacuum deposition, ion plating and electroplating are known as the most productive methods. It is generally said that these three deposition methods are difficult to be used for the production of alloy thin films. The reason for this is that while there is need to make a ratio among the evaporation rates of each alloy elements constant during the formation of an alloy thin film by vacuum deposition or ion plating, the vapor pressure of metal at a particular temperature greatly varies from one element to another, and so too does the evaporation rate.

Specifically, when an alloy evaporation source is heated and melted, only an element with higher vapor pressure (element A) first evaporates, and after element A has almost evaporated leaving little amount of element A in the evaporation source, the evaporation rate of an element with lower vapor pressure (element B) gradually increases and eventually only element B evaporates. Alloys with a controlled composition range cannot be obtained in such a process. While it has been known to alloy metals by means of annealing (heating) as disclosed by Patent Literature 7, annealing requires high temperature and therefore is not necessarily preferable because of the limited the choice of the substrate materials. For this reason, commonly, two or more separate evaporation sources are prepared, each of which contains one of the alloy elements. The heating temperature of each evaporation source is then independently controlled so as to control the evaporation rates of the alloy elements. Such a control scheme, of course, causes price increase in manufacturing equipment.

As shown in FIG. 1, copper and tin have very similar vapor pressure over a wide temperature range from 1,050° C. to 1,500° C. Thus, it has been established that even when a single copper-tin alloy evaporation source is used, it is possible to produce a copper-tin alloy deposited film with a relatively controlled alloy composition, in contrast to cases where alloy systems other than copper-tin alloy are used. The use of a single copper-tin alloy evaporation source is advantageous because cost reduction can be realized.

It should be noted, however, that the composition of the evaporation source does not necessary match the composition of the resultant deposited film; the composition of the deposition film is determined by various factors including specific gravity in melted state, in addition to vapor pressure of respective alloy metals. For this reason, it is difficult to predict the metal composition of the deposited thin film.

As a result of extensive studies, the inventors have also established that in copper-tin alloy systems, when the tin proportion is 15 atom % or more, the composition of the evaporation source becomes close to that of the deposited film. It is generally known that when deposition is continuously conducted using an alloy deposition source, some of the alloy elements predominantly evaporate and thereby the composition of the remaining evaporation source deviates from the original composition, so that the composition of the film being deposited likewise gradually deviates from the original composition. The inventors have also established that the amount of deviation in composition can be relatively reduced when the tin proportion in the deposited film is 15 atom % or more. For example, when the alloy deposition source contains 24 atom % to 33 atom % of tin, the composition of the deposited film at the start of the deposition process and the composition of the deposited film at the time where about two-third of the evaporation source has been consumed both satisfy the claimed ranges of antimicrobial metals. It is thus possible to efficiently form thin films of antimicrobial metal without having to perform any special additional step, such as adding any of the constituent metals during the deposition process.

A copper-tin alloy deposited film produced from a single alloy deposition source are not only cost-effective compared to those produced using two or more deposition sources, but tend to have a uniform alloy composition. Thus, in the present invention, it is preferable to form the copper-tin alloy layer by simultaneous vapor deposition using a single alloy deposition source. More specifically, the antimicrobial raw material of the present invention is preferably produced by the steps of: providing a deposition source consisting of copper-tin alloy; placing a substrate so as to face the deposition source; evaporating the deposition source to generate a metal vapor; allowing the metal vapor to contact the substrate to form thereon a copper-tin alloy layer. There is no particular limitation on the substrate; however, it is preferably resin which has a deflection temperature under load of 115° C. or below as measured in accordance with ASTM-D648-56 under a load of 1,820 kPa, natural fiber or paper.

The deposition source is preferably a copper-tin deposition source which contains over 60 atom % to 85 atom % of copper and 15 atom % to less than 40 atom % of tin. This is to obtain the above-described copper-tin alloy layer which contains over 60 atom % to 90 atom % of copper and 10 atom % to less than 40 atom % of tin.

Thus, there is no need to form thin films of respective alloy metals and to anneal the films for metal alloying as has been required by prior art. It is thus made possible to form a copper-tin alloy deposited film directly onto even a substrate layer with relatively low heat resistance.

When the antimicrobial raw material of the present invention is provided as a nonwoven fabric or woven fabric, it can be produced by depositing a thin film onto a resin film or paper, cutting the resultant thin film-deposited film or paper, and mixing it with other material. For example, a polyester film having a copper-tin alloy thin film deposited on the surface is cut into antimicrobial polyester slit yarn; yarn is spun from strands of the polyester slit yarn or from strands of the polyester slit yarn and other yarn; and strands of the obtained yarn or stands of the obtained yarn and other yarn are woven into fabric. In this way it is possible to readily obtain textile goods with controlled water absorbability, texture, hardness, durability, heat resistance, etc.

When the antimicrobial raw material of the present invention includes an additional layer, the substrate layer and addition layer may be layered on top of each other with any known layering method. Examples of the layering method include co-extrusion of the substrate layer and additional layer, and lamination. Lamination may be carried out using an adhesive or other agent as needed.

Antimicrobial paper can also be produced by cutting a copper-tin alloy thin film-deposited film or paper into pieces and mixing them with paper material. Antimicrobial raw material can also be produced by mixing, for example, crushed pieces of a substrate such as a copper-tin alloy thin film-deposited plastic film or copper-tin alloy thin film-deposited inorganic particles with plastic material, and molding the mixture into a desired shape by extrusion molding, injection molding, transfer molding or other method. These methods in which cut or crushed pieces of a copper-tin alloy thin film-deposited substrate are formulated upon article manufacturing have the advantage of being capable of readily producing antimicrobial articles of various forms. On the other hand, since articles produced in this way are not entirely covered with copper-tin alloy on their surface, they have lower surface antimicrobial effect than those entirely covered with copper-tin alloy on their surface.

3. Application of Antimicrobial Raw Material

As described above, the antimicrobial raw material of the present invention has high antimicrobial activity and high corrosion resistance. For this reason, the antimicrobial raw material of the present invention is preferably used as various antimicrobial materials. Examples of antimicrobial materials include medical materials, home materials, purification materials, agricultural materials, and various surface protection films.

Examples of the medical materials include medical devices, drug containers, personal protectors for infection prevention (including masks etc.), dressings, wound dressing films, and adhesive bandages. Examples of the home materials include storage containers or packaging materials for food, drinking water, domestic water, flowers and ornamental plants; kitchen materials such as cutting boards and food refuse catching materials; bathroom materials such as washbasin and bathroom seats; cleaning materials such as dishcloths and dustcloths; garment materials such as clothes, footwear and bag; residence materials such as curtain, matting, and bedding; sanitary materials such as masks, simple toilet bowls, toilet seats, disposable diapers and sanitary protection products. Examples of the purification materials include gas cleaning filters and fluid cleaning filters. Examples of the agricultural materials include multi-sheets, filters for hydroponic culture, sheets for seedling boxes, fruit covers, and light reflective sheets for fruit coloring. Examples of the surface protection films include touch panel protection films which are attached to the touch-panel screen of displays.

The antimicrobial raw material of the present invention can also be processed into suitable shape as needed for use as building materials to be attached to the surface of various buildings. Examples of such building materials include those attached to rest rooms, bathrooms, shower rooms, laundry rooms and kitchens of facilities; cooking rooms of food-handling facilities; the boundary between the general ward isolation ward in medical facilities, rooms in front of intensive care units, and medical devices; rooms in front of cleaning rooms of semiconductor mills; building structures such as entrance and footgear room of buildings, or the wall, floor or fitting frame or the surface of doors, windows, handrails, electrical switches, kitchen counters, sinks, cocks, bathtubs, toilet bowls, furniture, and fixtures installed to them.

EXAMPLES

Hereinafter, the present invention will be described in detail with reference to Examples and Comparative Examples, which however shall not be construed as limiting the scope of the invention.

Example 1

As a substrate film, a 50 μm-thick biaxially stretched polypropylene film (Mitsui Chemicals Tohcello, Inc., deflection temperature under load (1,820 kPa): 57° C. to 63° C.) is provided. The substrate film is loaded 400 mm above the evaporation source in a evaporator.

18.0 g of pure copper (purity: 99.9%) particles of 1-2 mm size and 12.0 g of pure tin (purity: 99.9%) particles of 1-2 mm size (total: 30 g) are weighted into a metallic container and thoroughly mixed to prepare an evaporation source consisting of 74 atom % (60 wt %) copper and 26 atom % (40 wt %) tin. The evaporation source is placed in a melting pot of the evaporator, and the apparatus is vacuumed to a pressure of $10^{-3}$ Pa or less. Subsequently, in order to avoid excessive scattering of the evaporation source, the melting pot and evaporation source are slowly heated with electron beams, completely melting the evaporation source in the melting pot to prepare an alloy evaporation source. After allowing the alloy evaporation source to stand for cooling in vacuum, the evaporation source is again heated with electron beams to deposit a copper-tin alloy thin film onto the substrate film placed about 400 mm above the evaporation source. Deposition rate is set to 10 nm to 15 nm per second. The obtained copper-tin alloy thin film is 50±10 nm in thickness.

Examples 2 to 5

Copper-tin alloy thin films are formed on substrate films in the same manner as in Example 1 except that tin proportion in the evaporation source is changed as shown in Table 1 while ensuring that the total amount of metals charged to prepare the evaporation source is 30 g.

Example 6

A copper-tin-aluminum alloy thin film is formed on a substrate film in the same manner as in Example 1 except that 18.0 g of pure copper (purity: 99.9%) particles of 1-2 mm size, 6.0 g of pure tin (purity: 99.9%) particles of 1-2 mm size, and 6.0 g of pure aluminum (purity: 99.9%) particles of 3-5 mm size (total: 30 g) are weighted to prepare an alloy evaporation source with a metal composition of 51 atom % (60 wt %) copper, 9 atom % (20 wt %) tin and 40 atom % (20 wt %) aluminum.

Example 7

As a substrate film, a 50 μm-thick biaxially stretched polypropylene film (Mitsui Chemicals Tohcello, Inc., deflection temperature under load (1,820 kPa) of 57° C. to 63° C.) is provided. The substrate film is loaded into a DC sputtering apparatus.

Pure copper (purity: 99.99%) sputtering target and pure tin (purity: 99.99%) sputtering target are also loaded into the DC sputtering apparatus. After adjusting the level of direct current to be applied to each target such that an alloy thin film consists of 90 atom % copper and 10 atom % tin, a copper-tin alloy thin film is deposited onto the substrate film. The copper-tin alloy thin film thus obtained is 50 nm in thickness.

Examples 8 and 9

Copper-tin alloy thin films are formed on substrate films in the same manner as in Example 7 except that the level of direct current applied to the target is adjusted such that the tin proportion in the resulting alloy thin film has the value shown in Table 2.

Example 10 and Comparative Example 19

Copper-tin alloy thin films are formed on substrate films in the same manner as in Example 1 except that the copper-tin alloy thin films are vapor-deposited such that the tin proportion in the alloy thin film and film thickness are as shown in Table 2.

Example 11 and Comparative Example 20

Copper-tin alloy thin films are formed on substrate films in the same manner as in Example 7 except that alloy thin films are sputter-deposited such that the tin proportion in the alloy thin film and film thickness are as shown in Table 2.

Comparative Example 1

A copper-tin alloy thin film is formed on a substrate film in the same manner as in Example 1 except that 24.0 g of pure copper (purity: 99.9%) particles of 1-2 mm size and 6.0 g of pure tin (purity: 99.9%) particles of 1-2 mm size are weighted to prepare an alloy evaporation source with a metal composition of 88 atom % (80 wt %) copper and 12 atom % (20 wt %) tin.

Comparative Example 2

A copper-tin alloy thin film is formed on a substrate film in the same manner as in Example 1 except that the tin proportion in the alloy evaporation source is changed as shown in Table 3.

Comparative Example 3

A copper-aluminum alloy thin film is vapor-deposited onto a substrate film in the same manner as in Example 1 except that 25.5 g of pure copper (purity: 99.9%) particles of 1-2 mm size and 4.5 g of pure aluminum (purity: 99.9%) particles of 3-5 mm size (total: 30 g) are weighted to prepare an alloy evaporation source with a metal composition of 70 atom % (85 wt %) copper and 30 atom % (15 wt %) aluminum.

Comparative Example 4

A copper-aluminum alloy thin film is vapor-deposited onto a substrate film in the same manner as in Comparative Example 3 except that the aluminum proportion in the alloy evaporation source is changed as shown in Table 3.

Comparative Example 5

A copper-germanium alloy thin film is vapor-deposited onto a substrate film in the same manner as in Example 1 except that 20.0 g of pure copper (purity: 99.9%) particles of 1-2 mm size and 10.0 g of irregular pieces of pure germanium (purity: 99.9%) (total: 30 g) are weighted to prepare an alloy evaporation source with a metal composition of 70 atom % (67 wt %) copper and 30 atom % (33 wt %) germanium.

Comparative Example 6

A copper-germanium alloy thin film is vapor-deposited onto a substrate film in the same manner as in Comparative Example 5 except that the germanium proportion in the alloy evaporation source is changed as shown in Table 3.

Comparative Example 7

A 3 mm-diameter brass rod (30.0 g) consisting of 60 wt % copper and 40 wt % zinc is prepared as an evaporation source. To prepare a massive alloy evaporation source as in Example 1, the evaporation source is heated for melting, but a colorless metal film is deposited onto the window of the evaporator before melting of the evaporation source occurs. Further, an alloy thin film is vapor-deposited onto a substrate film in the same manner as in Example 1. However, the resultant thin film and the remaining evaporation source both have the same color as pure copper.

Comparative Example 8

A brass sputtering target (60 wt % copper and 40 wt % zinc) is loaded into a DC sputtering apparatus. A 50 nm-thick alloy thin film is then formed on a substrate film by sputtering.

Comparative Example 9

A copper-silicon alloy thin film is vapor-deposited onto a substrate film in the same manner as in Example 1 except that 25.2 g of pure copper (purity: 99.99%) particles of 1-2 mm size and 4.8 g of irregular pieces of pure silicon (purity: 99.99%) (total: 30 g) are weighted to prepare an alloy evaporation source with a metal composition of 70 atom % (84 wt %) copper and 30 atom % (16 wt %) silicon. The resultant alloy thin film has the same color as pure copper.

Comparative Example 10

A tin thin film is formed on a substrate film in the same manner as in Example 1 except that 30 g of pure tin (purity: 99.9%) particles of 1-2 mm size is weighted to prepare an evaporation source.

Comparative Example 11

A copper thin film is formed on a substrate film in the same manner as in Example 1 except that 30 g of pure copper (purity: 99.9%) particles of 1-2 mm size is weighted to prepare an evaporation source.

Comparative Example 12

A pure copper sputtering target (purity: 99.99%) is loaded into a DC sputtering apparatus. A 50 nm-thick copper thin film is then deposited onto a substrate film by sputtering.

Comparative Example 13

A silver thin film is formed on a substrate film in the same manner as in Example 1 except that 30 g of pure silver (purity: 99.9%) particles of 1-2 mm size is weighted to prepare an evaporation source.

Comparative Example 14

A pure silver sputtering target (purity: 99.99%) is loaded into a DC sputtering apparatus. A 50 nm-thick silver thin film is then deposited onto a substrate film by sputtering.

Comparative Examples 15 and 16

Copper-tin alloy thin films are formed on substrate films in the same manner as in Comparative Examples 1 and 2 except that the copper-tin alloy thin films are subjected to annealing at 200° C. for 2 hours in an oven.

Comparative Example 17

A copper-tin alloy thin film is formed on a substrate film in the same manner as in Example 1 except that the copper-tin alloy thin film is formed by vapor deposition such that the tin proportion in the resultant alloy thin film and its thickness are as shown in Table 5.

Comparative Example 18

A copper-tin alloy thin film is formed on a substrate film in the same manner as in Example 7 except that the copper-tin alloy thin film is deposited by sputtering such that the tin proportion in the resultant alloy thin film and its thickness are as shown in Table 5.

1) Q value, 2) surface smoothness and 3) XRD of the thin films of some of Examples and Comparative Examples are measured as described below.

1) Q Value

The films prepared in Examples 10 to 11 and Comparative Examples 12, 17 to 20 are cut into pieces of given size to prepare sample films. The electrodes of four terminals composed of current source terminals of an electric current feeder and of voltage detection terminals of a voltage meter are pressed against the thin film surface of each sample film. Sheet resistance is then measured using the DC four terminal method, by applying the following direct currents to the thin film surface of the sample film and measuring the change in voltage.

Direct current: $1\times10^{-6}$ (A), $2\times10^{-6}$ (A), $5\times10^{-6}$ (A), $1\times10^{-5}$ (A), $2\times10^{-5}$ (A), $2\times10^{-5}$ (A).

Current supply equipment: KEITHLEY220 PROGRAMMABLE CURRENT SOURCE

Voltage application equipment: KETHLEY196 SYSTEM DMM is used.

Q value (Ω/(nm·Cu atom %)) is obtained by dividing sheet resistance (Ω) by a product of film thickness (nm) and copper atom content.

2) Surface Smoothness

The films prepared are cut into pieces of given size to prepare sample films. The surface smoothness (unit: nm) of the thin film of each sample film is measured with a Detak-III surface profiler (ULVAC) under the following condition:

Load: 25 mg

Needle: diamond needle of 12.5 μm radius

3) XRD

The films prepared are cut into pieces of given size to prepare sample films. XRD of the thin film of each sample film is measured with a X-ray diffractometer (Rigaku, RINT 1500) under the following condition:

X ray target: Cu

X-ray: Cu K ALPHA1

Goniometer: wide angle goniometer

Scan speed: 2° / min

Scan step: 0.02°

Scan range: 3 to 100°

Figure 2A:
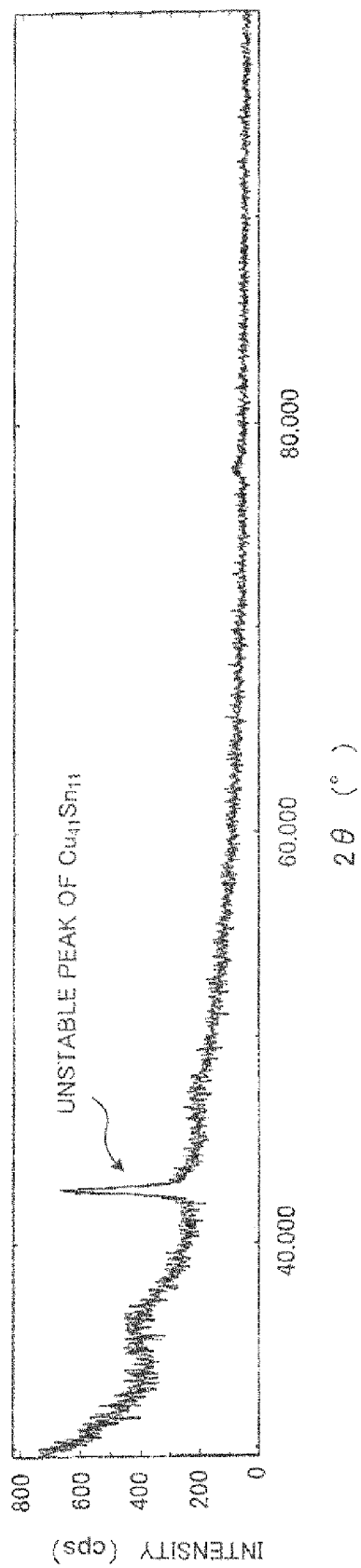
FIG. 2 shows XRD measurements in Examples.
Figure 2B:
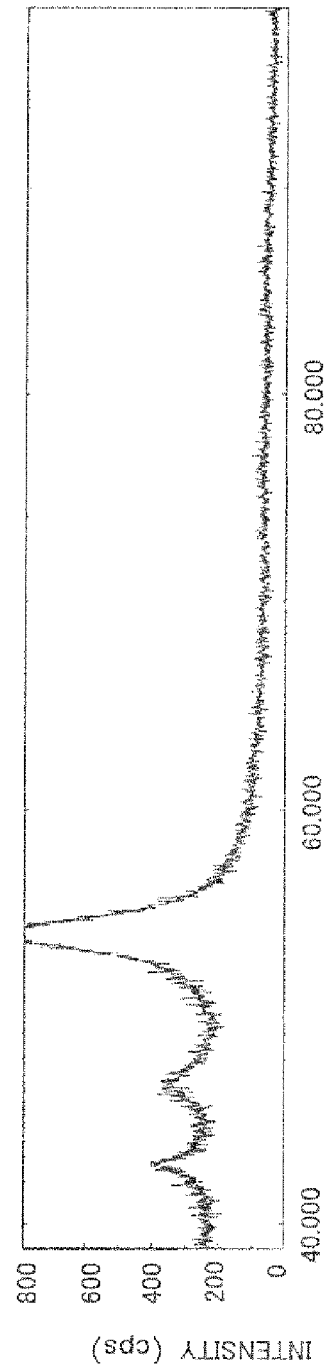

FIG. 2A shows XRD data of a vapor-deposited film of Example 1, and FIG.2B shows XRD data of a sputter-deposited film of Example 11. In FIG. 2 the horizontal axis represents 2 θ(°) (where θ is incident angle), and the vertical axis represents intensity (cps).

The following Tests A to D are conducted for the films prepared in Examples 1 to 9 and Comparative Examples 1 to 14. Tests E and F are also conducted for some of the films as well as for the films prepared in Comparative Examples 15 and 16.

Test A (Metal Composition Analysis)

A part of each film is cut into an approximately 3 mm square piece to prepare a sample film. Metal atoms contained in the thin film of the sample film are detected by energy dispersive spectroscopy (EDS) to measure the atomic proportion of the doped metal other than copper (e.g., tin in Example 1) among all of the detected metals.

Test B (antimicrobial activity test)

The films prepared are cut into 50 mm square pieces to prepare sample films. Antimicrobial activity test against *Staphylococcus aureus* is conducted for these sample films in accordance with JIS Z 2801.

Colony counts for the bacteria detected after the test are given in Tables 1 to 5 as colony count (A) measured 24 hour after the test. Note that the absence of any bacteria is denoted as "<10" in Tables 1 to 5. Values of the common logarithm of the quotient of colony count for the bacteria detected on a polyethylene plate as a control article and colony count (A) are also given in Tables 1 to 5 as values for antimicrobial activity. Note that the test is split into multiple sessions. Since each session has a different colony count for control, some of the sample films show the same antimicrobial activity even when they have different values for colony count (A).

Test C (Durability Test: Degradation by Contact with Hot Water)

The films prepared are cut into 50 mm square pieces to prepare sample films, and are attached to the wall of a bathroom. After showering the surface of the sample films with 40±2° C. hot water for 30 seconds with a hand shower, 40±2° C. hot water droplets are splashed against the film surface, and the sample films are allowed to stand for drying without wiping off the water droplets attached. This procedure is conducted for 3 days twice per day, after which the degree of degradation of the metal thin film is visually evaluated. The same procedure is then conducted for a further 4 days, and then the degree of degradation of the metal thin film (7 days in total) is visually evaluated.

The degree of degradation of the metal thin film is evaluated in terms of the occurrence of discoloration and the presence or absence of film loss (peeling) of the metal thin film.

(Discoloration)
O: No discoloration in metal thin film
x: Discoloration in metal thin film
(Film Loss)
Evaluation is made by judging whether or not film peeling occurs (specifically, whether or the substrate layer is exposed and visible) after peeling a double-faced adhesive tape attached to the metal thin film.
O: No film loss (peeling) in metal thin film
x: Film loss in metal thin film Test D (Durability Test: Degradation by Contact with Salt Water)

The films prepared are cut into 50 mm square pieces to prepare sample films. The surface of the sample films is wiped with a loosely squeezed saline-wetted gauze three times under a pressing load of 2±0.5N, and the sample films are allowed to stand for drying without wiping off water droplets attached. This procedure is conducted for 3 days twice per day, after which the degree of degradation of the metal thin film is visually evaluated. The same procedure is then conducted for a further 4 days, and then the degree of degradation of the metal thin film (7 days in total) is visually evaluated.

The degree of degradation of the metal thin film is evaluated in terms of the occurrence of discoloration and the presence or absence of film loss (peeling) of the metal thin film.
(Discoloration)
O: No discoloration in metal thin film
x: Discoloration in metal thin film
(Film Loss)
Evaluation is made by judging whether or not film peeling occurs (specifically, whether or the substrate layer is exposed and visible) after peeling a double-faced adhesive tape attached to the metal thin film.
O: No film loss (peeling) in metal thin film
x: Film loss in metal thin film Test E (Curvature)

A 25 μm-thick biaxially stretched polypropylene film is cut into a 4 cm×10 cm piece to prepare a sample film. A 50 nm-thick thin film is deposited onto the sample film. The amount of curvature (mm) of the film sample is measured from the surface of the film sample prior to thin film deposition after allowing it stand at 23° C. at 50% RH for 24 hours. The amount of curvature of the film sample is measured as the mean value of the vertical distances of the lengthwise ends of film from the horizontal surface.

Test F (Abrasion Resistance Test)

Figure 3:
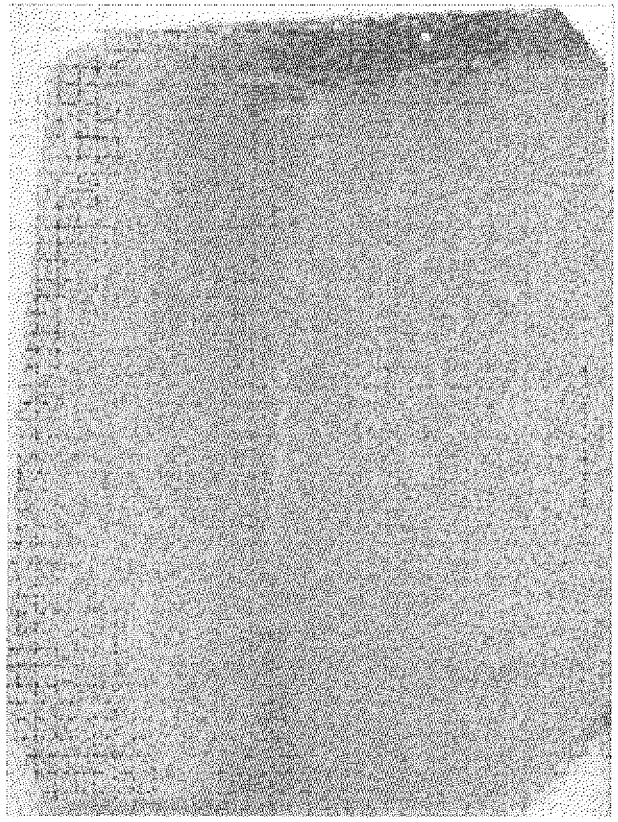
FIG. 3 is a picture showing the surface of a metal thin film of Example after abrasion resistance test.

A 50 nm-thick thin film is deposited onto a sample film which is obtained by cutting a 25 μm-thick biaxially stretched polypropylene into a 4 cm×10 cm piece. The surface of the thin film on the sample film is scratched with a water-wetted felt cloth under a load of 3 kgf, and the number of scratches it takes until the color of the underlying substrate layer becomes visible is counted. The larger number of scratches it takes until the color of the substrate layer becomes visible means higher abrasion resistance of the thin film. FIG. 3 shows the surface state of the thin film of the sample film of Example 1 after it has been scratched 30 times.

The evaluations results of Examples 1 to 6 are given in Table 1, the evaluation results of Examples 7 to 11 and Comparative Examples 19 to 20 are given in Table 2, the evaluation results of Comparative Examples 1 to 6 are given in Table 3, the evaluation results of Comparative Examples 7 to 12 are given in Table 4, and the evaluation results of Comparative Examples 13 to 18 are given in Table 5. Note in Tables 1 to 5 that the film composition and evaporation source composition represent metal content (atom %) other than copper. For example, [Sn:20] means [Cu/Sn=80 atom %/20 atom %]. Non-tested items are designated as [—].

TABLE 1

| | | | Ex. 1 | Ex. 2 | Ex. 3 | Ex. 4 | Ex. 5 | Ex. 6 |
|---|---|---|---|---|---|---|---|---|
| Film structure | Substrate layer | Material | PP | PP | PP | PP | PP | PP |
| | | DTUL (@1820 kPa) (° C.) | 57-63 | 57-63 | 57-63 | 57-63 | 57-63 | 57-63 |
| | | Thickness (μm) | 50 | 50 | 50 | 50 | 50 | 50 |
| | Metal layer | Film composition (atom % of metal other than Cu) | Sn: 20 | Sn: 15 | Sn: 12 | Sn: 28 | Sn: 36 | Sn/Al: 21/29 |
| | | Sheet resistance per unit volume (Ω/nm) | — | — | — | — | — | — |
| | | Surface smoothness (nm) | 7.6 | 14.2 | — | — | — | — |
| | | Thickness (nm) | 50 | 50 | 50 | 50 | 50 | 50 |
| Deposition condition | | Deposition method | Vacuum deposition | Vacuum deposition | Vacuum deposition | Vacuum deposition | Vacuum deposition | Vacuum deposition |
| | | Evaporation source composition (atom % of metal other than Cu) | Sn: 26 | Sn: 23 | Sn: 19 | Sn: 31 | Sn: 39 | Sn/Al: 9/40 |
| | | Annealing | Not conducted | Not conducted | Not conducted | Not conducted | Not conducted | Not conducted |
| Evaluation | Antimicrobial activity test | Bacteria count after 24 h (cfu/25 cm²) | <10 | <10 | <10 | <10 | <10 | <10 |
| | | Antimicrobial activity | >4 | >4 | >4 | >4 | >4 | >4 |
| | Durability test (hot water contact) | 3 day after Discoloration | O | O | O | O | O | O |
| | | Film loss | O | O | O | O | O | O |
| | | 7 day after Discoloration | O | O | O | O | O | O |
| | | Film loss | O | O | X | O | O | O |
| | Durability test (salt water contact) | 3 day after Discoloration | O | O | O | O | O | O |
| | | Film loss | O | O | O | O | O | O |
| | | 7 day after Discoloration | O | O | O | O | O | O |
| | | Film loss | O | O | X | O | O | O |
| | | Curvature[note] (mm) | 0 | 0 | — | — | — | — |
| | | Abrasion resistance[note] (number of scratches) | 60 | 60 | — | — | — | — |

[note]value where 25-μm thick polypropylene (PP) film is used as substrate layer

TABLE 2

| | | | Ex. 7 | Ex. 8 | Ex. 9 | Ex. 10 | Comp Ex. 19 | Ex. 11 | Comp Ex. 20 |
|---|---|---|---|---|---|---|---|---|---|
| Film structure | Substrate layer | Material | PP | PP | PP | PP | PP | PP | PP |
| | | DTUL (@1820 kPa) (° C.) | 57-63 | 57-63 | 57-63 | 57-63 | 57-63 | 57-63 | 57-63 |
| | | Thickness (μm) | 50 | 50 | 50 | 50 | 50 | 50 | 50 |
| | Metal layer | Film composition (atom % of metal other than Cu) | Sn: 10 | Sn: 15 | Sn: 37 | Sn: 30 | Sn: 40 | Sn: 30 | Sn: 40 |
| | | Sheet resistance per unit volume (Ω/nm) | — | — | — | 0.165 | 0.091 | 0.566 | 0.648 |
| | | Surface smoothness (nm) | — | 8.5 | 6.3 | — | — | — | — |
| | | Thickness (nm) | 50 | 50 | 50 | 50 | 35 | 25 | 25 |
| Deposition condition | | Deposition method | sputtering | sputtering | sputtering | Vacuum deposition | Vacuum deposition | sputtering | sputtering |
| | | Evaporation source composition (atom % of metal other than Cu) | — | — | — | Sn: 30 | Sn: 42 | — | — |
| | | Annealing | Not conducted | Not conducted | Not conducted | Not conducted | Not conducted | Not conducted | Not conducted |
| Evaluation | Antimicrobial activity test | Bacteria count after 24 h (cfu/25 cm$^2$) | <10 | <10 | <10 | — | — | — | — |
| | | Antimicrobial activity | >4 | >4 | >4 | — | — | — | — |
| | Durability test (hot water contact) | 3 day after Discoloration | ○ | ○ | ○ | — | — | — | — |
| | | Film loss | ○ | ○ | ○ | — | — | — | — |
| | | 7 day after Discoloration | ○ | ○ | ○ | — | — | — | — |
| | | Film loss | X | ○ | ○ | — | — | — | — |
| | Durability test (salt water contact) | 3 day after Discoloration | ○ | ○ | ○ | — | — | — | — |
| | | Film loss | ○ | ○ | ○ | — | — | — | — |
| | | 7 day after Discoloration | ○ | ○ | ○ | — | — | — | — |
| | | Film loss | X | ○ | ○ | — | — | — | — |
| | Curvature[note] (mm) | | — | 0 | 0 | — | — | — | — |
| | Abrasion resistance[note] (number of scratches) | | — | 30 | 30 | — | — | — | — |

[note] value where 25-μm thick polypropylene (PP) film is used as substrate layer

TABLE 3

| | | | Comp. Ex. 1 | Comp. Ex. 2 | Comp. Ex. 3 | Comp. Ex. 4 | Comp. Ex. 5 | Comp. Ex. 6 |
|---|---|---|---|---|---|---|---|---|
| Film structure | Substrate layer | Material | PP | PP | PP | PP | PP | PP |
| | | DTUL (@1820 kPa) (° C.) | 57-63 | 57-63 | 57-63 | 57-63 | 57-63 | 57-63 |
| | | Thickness (μm) | 50 | 50 | 50 | 50 | 50 | 50 |
| | Metal layer | Film composition (atom % of metal other than Cu) | Sn: 4 | Sn: 40 | Al: 22 | Al: 50 | Ge: 12 | Ge: 36 |
| | | Sheet resistance per unit volume (Ω/nm) | — | — | — | — | — | — |
| | | Surface smoothness (nm) | — | — | — | — | — | — |
| | | Thickness (nm) | 50 | 50 | 50 | 50 | 50 | 50 |
| Deposition condition | | Deposition method | Vacuum deposition | Vacuum deposition | Vacuum deposition | Vacuum deposition | Vacuum deposition | Vacuum deposition |
| | | Evaporation source composition (atom % of metal other than Cu) | Sn: 12 | Sn: 45 | Al: 30 | Al: 50 | Ge: 30 | Ge: 50 |
| | | Annealing | Not conducted | Not conducted | Not conducted | Not conducted | Not conducted | Not conducted |
| Evaluation | Antimicrobial activity test | Bacteria count after 24 h (cfu/25 cm$^2$) | <10 | 87000 | <10 | <10 | <10 | <10 |
| | | Antimicrobial activity | >4 | 0.9 | >4 | >4 | >4 | >4 |
| | Durability test (hot water contact) | 3 day after Discoloration | ○ | ○ | ○ | ○ | X | X |
| | | Film loss | X | ○ | X | X | X | X |
| | | 7 day after Discoloration | ○ | ○ | ○ | ○ | X | X |
| | | Film loss | X | ○ | X | X | X | X |
| | Durability test (salt water contact) | 3 day after Discoloration | X | ○ | X | X | X | X |
| | | Film loss | X | ○ | X | X | X | X |
| | | 7 day after Discoloration | X | ○ | X | X | X | X |
| | | Film loss | X | ○ | X | X | X | X |

TABLE 3-continued

|  | Comp. Ex. 1 | Comp. Ex. 2 | Comp. Ex. 3 | Comp. Ex. 4 | Comp. Ex. 5 | Comp. Ex. 6 |
|---|---|---|---|---|---|---|
| Curvature[note] (mm) | — | — | — | — | — | — |
| Abrasion resistance[note] (number of scratches) | — | — | — | — | — | — |

[note]value where 25-μm thick polypropylene (PP) film is used as substrate layer

TABLE 4

| | | | Comp. Ex. 7 | Comp. Ex. 8 | Comp. Ex. 9 | Comp. Ex. 10 | Comp. Ex. 11 | Comp. Ex. 12 |
|---|---|---|---|---|---|---|---|---|
| Film structure | Substrate layer | Material | PP | PP | PP | PP | PP | PP |
| | | DTUL (@1820 kPa) (° C.) | 57-63 | 57-63 | 57-63 | 57-63 | 57-63 | 57-63 |
| | | Thickness (μm) | 50 | 50 | 50 | 50 | 50 | 50 |
| | Metal layer | Film composition (atom % of metal other than Cu) | Zn: <1 | Zn: 34 | Si: <1 | Sn: 100 | Cu: 100 | Cu: 100 |
| | | Sheet resistance per unit volume (Ω/nm) | — | — | — | — | — | — |
| | | Surface smoothness (nm) | — | — | — | — | — | 22.3 |
| | | Thickness (nm) | 50 | 50 | 50 | 50 | 50 | 50 |
| Deposition condition | | Deposition method | Vacuum deposition | Sputtering | Vacuum deposition | Vacuum deposition | Vacuum deposition | Sputtering |
| | | Evaporation source composition (atom % of metal other than Cu) | Zn: 34 | Zn: 34 | Si: 30 | Sn: 100 | (Cu: 100) | (Cu: 100) |
| | | Annealing | Not conducted | Not conducted | Not conducted | Not conducted | Not conducted | Not conducted |
| Evaluation | Antimicrobial activity test | Bacteria count after 24 h (cfu/25 cm²) | <10 | <10 | <10 | 18000 | <10 | <10 |
| | | Antimicrobial activity | >4 | >4 | >4 | 0.9 | >4 | >4 |
| | Durability test (hot water contact) | 3 day after Discoloration | ○ | ○ | ○ | ○ | ○ | ○ |
| | | Film loss | X | X | X | ○ | X | X |
| | | 7 day after Discoloration | ○ | ○ | ○ | ○ | ○ | ○ |
| | | Film loss | X | X | X | ○ | X | X |
| | Durability test (salt water contact) | 3 day after Discoloration | X | X | X | ○ | X | X |
| | | Film loss | X | X | X | ○ | X | X |
| | | 7 day after Discoloration | X | X | X | ○ | X | X |
| | | Film loss | X | X | X | ○ | X | X |
| | Curvature[note] (mm) | | — | — | — | — | — | 0 |
| | Abrasion resistance[note] (number of scratches) | | — | — | — | — | — | 10 |

[note]value where 25-μm thick polypropylene (PP) film is used as substrate layer

TABLE 5

| | | | Comp. Ex. 13 | Comp. Ex. 14 | Comp. Ex. 15 | Comp. Ex. 16 | Comp. Ex. 17 | Comp. Ex. 18 |
|---|---|---|---|---|---|---|---|---|
| Film structure | Substrate layer | Material | PP | PP | PP | PP | PP | PP |
| | | DTUL (@1820 kPa) (° C.) | 57-63 | 57-63 | 57-63 | 57-63 | 57-63 | 57-63 |
| | | Thickness (μm) | 50 | 50 | 50 | 50 | 50 | 50 |
| | Metal layer | Film composition (atom % of metal other than Cu) | Ag: 100 | Ag: 100 | Sn: 4 | Sn: 40 | Sn: 50 | Sn: 50 |
| | | Sheet resistance per unit volume (Ω/nm) | — | — | — | — | 0.0172 | 0.230 |
| | | Surface smoothness (nm) | — | — | 23.1 | 20.9 | — | — |
| | | Thickness (nm) | 50 | 50 | 50 | 50 | 55 | 25 |
| Deposition condition | | Deposition method | Vacuum deposition | Sputtering | Vacuum deposition | Vacuum deposition | Vacuum deposition | Sputtering |
| | | Evaporation source composition (atom % of metal other than Cu) | Ag: 100 | Ag: 100 | Sn: 12 | Sn: 45 | Sn: 60 | — |
| | | Annealing | Not conducted | Not conducted | Conducted | Conducted | Not conducted | Not conducted |

TABLE 5-continued

|  |  |  | Comp. Ex. 13 | Comp. Ex. 14 | Comp. Ex. 15 | Comp. Ex. 16 | Comp. Ex. 17 | Comp. Ex. 18 |
|---|---|---|---|---|---|---|---|---|
| Evaluation | Antimicrobial activity test | Bacteria count after 24 h (cfu/25 cm²) | <10 | <10 | — | — | — | — |
|  |  | Antimicrobial activity | >4 | >4 | — | — | — | — |
|  | Durability test (hot water contact) | 3 day after Discoloration | ○ | ○ | — | — | — | — |
|  |  | Film loss | ○ | ○ | — | — | — | — |
|  |  | 7 day after Discoloration | ○ | ○ | — | — | — | — |
|  |  | Film loss | ○ | ○ | — | — | — | — |
|  | Durability test (salt water contact) | 3 day after Discoloration | X | X | — | — | — | — |
|  |  | Film loss | X | X | — | — | — | — |
|  |  | 7 day after Discoloration | X | X | — | — | — | — |
|  |  | Film loss | X | X | — | — | — | — |
|  |  | Curvature[note] (mm) | — | — | 3 | 3 | — | — |
|  |  | Abrasion resistance[note] (number of scratches) | — | — | 100 | 100 | — | — |

[note]value where 25-μm thick polypropylene (PP) film is used as substrate layer From the evaluation results of Examples 1 to 9 given in Tables 1 and 2 and the evaluation results of Comparative Examples 1 to 14 given in Tables 3 to 5, it can be seen that the films having the copper-tin alloy thin films of Examples 1 to 9 have sufficiently higher antimicrobial activity than those of Comparative Examples 1 to 14. It can also be seen that the films having the copper-tin alloy thin films of Examples 1 to 9 showed no discoloration or film loss both after the 3-day degradation test by hot water showering and the 3-day degradation by salt water contact, thus showing superior corrosion resistance compared to the films having the copper-tin alloy thin films of Comparative Examples 1 to 14. It can be particularly seen that the films having the copper-tin thin films containing 15 atom % or more of tin showed no discoloration or film loss even after the 7-day degradation test by hot water showering and after the 7-day degradation by salt water contact, thus showing much higher corrosion resistance.

Comparison of Examples 1, 2, 8 and 9 with Comparative Examples 15 and 16 reveals that the amount of film curvature can be significantly reduced when annealing treatment is not conducted.

Comparison of Example 10 with Example 11 reveals that the vapor-deposited alloy thin films have smaller Q value than the sputter-deposited alloy thin films and thus are less dense (i.e., sparse). It can also be seen that the vapor-deposited alloy thin films have high abrasion resistance as well as superior film strength and adhesion to substrate film compared to the sputter-deposited alloy thin films. As shown in FIG. 3, it can be seen that the color of the substrate layer is not yet confirmed after scratching the thin film surface of the sample film of Example 1 30 times.

From the XRD data shown in FIG. 2, it is confirmed that the unstable peak of $Cu_{41}Sn_{11}$ is more intense for the vapor-deposited alloy thin films than for the sputter-deposited alloy thin films. It can be seen that alloy thin film abrasion resistance increases with increasing intensity of the unstable peak of $Cu_{41}Sn_{11}$. The relatively large peak confirmed in FIG. 2B is considered to be a peak derived from the substrate (PET).

This application is entitled and claims the priority of Japanese Patent Application No. 2009-206818 filed on Sep. 8, 2009, the disclosure of each of which including the specification, drawings and abstract is incorporated herein by reference in its entirety.

Industrial Applicability

According to the present invention, it is possible to relatively inexpensively provide an antimicrobial raw material which has high antimicrobial activity and high corrosion resistance and which can be directly deposited even onto low-heat resistant plastic substrates. Thus, the antimicrobial raw material can be suitably used as a flexible antimicrobial raw material.

The invention claimed is:

1. An antimicrobial raw material comprising:
a substrate layer made of resin, natural fiber or paper, the resin having a deflection temperature under load of 115° C. or below as measured in accordance with ASTM-D648-56 under a load of 1,820 kPa; and
a copper-tin alloy layer disposed on the substrate layer, the copper-tin alloy layer containing 10 atom % to less than 40 atom % of tin, with remaining portion substantially consisting of copper,
wherein the copper-tin alloy layer has a thickness of 5 nm to 200 nm; and
the copper-tin alloy layer has Q value ($\Omega$/(nm·Cu atom %)) of 0.001 to 0.007, the Q value being obtained by dividing a sheet resistance ($\Omega$) of the copper-tin alloy layer by a product of thickness of (nm) and copper atom content (Cu atom %) of the copper-tin alloy layer.

2. The antimicrobial raw material according to claim 1, wherein the copper-tin alloy layer contains 15 atom % to less than 40 atom % of tin, with the remaining portion substantially consisting of copper.

3. The antimicrobial raw material according to claim 1, wherein the substrate layer is made of material selected from the group consisting of polyethylene terephthalate, polyethylene naphthalate, polyethylene, and polypropylene.

4. The antimicrobial raw material according to claim 1, wherein the copper-tin alloy layer forms the entire or part of an outermost surface of the antimicrobial raw material.

5. The antimicrobial raw material according to claim 1, wherein the antimicrobial raw material is a film, and when the film is 4 cm in width, 10 cm in length and 25 μm in thickness, an amount of curvature is 2 mm or less.

6. The antimicrobial raw material according to claim 1, wherein the substrate layer is a nonwoven fabric, woven fabric or yarn.

7. An antimicrobial material comprising the antimicrobial raw material according to claim 1.

8. A method for producing an antimicrobial raw material, comprising:
- providing an evaporation source composed of an copper-tin alloy containing over 60 atom % to 85 atom % of copper and 15 atom % to less than 40 atom % of tin;
- placing a substrate so as to face the evaporation source wherein the substrate is made of resin, natural fiber or paper, the resin having a deflection temperature under load of 115° C. or below as measured in accordance with ASTM-D648-56 under a load of 1,820 kPa;
- evaporating the copper-tin alloy from the evaporation source to generate a metal vapor; and
- allowing the metal vapor to contact the substrate to deposit thereon a copper-tin alloy layer containing over 60 atom % to 90 atom % of copper and 10 atom % to less than 40 atom % of tin,
- the copper-tin alloy layer having Q value ($\Omega$/(nm·Cu atom %)) of 0.001 to 0.007, the Q value being obtained by dividing a sheet resistance ($\Omega$) of the copper-tin alloy layer by a product of thickness of (nm) and copper atom content (Cu atom %) of the copper-tin alloy layer.

9. The antimicrobial material according to claim 7, wherein the antimicrobial material is used as a touch panel protection film.

10. The antimicrobial material according to claim 7, wherein the antimicrobial material is used as medical material.

11. The antimicrobial material according to claim 7, wherein the antimicrobial material is used as purification material.

* * * * *